(12) United States Patent
Olson et al.

(10) Patent No.: US 6,692,745 B2
(45) Date of Patent: *Feb. 17, 2004

(54) COMPOSITIONS AND METHODS FOR INHIBITION OF HIV-1 INFECTION

(75) Inventors: William C. Olson, Ossining, NY (US); Paul J. Maddon, Scarsdale, NY (US)

(73) Assignee: Arogenics Pharmaceuticals, Inc., Tarrytown, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/493,346

(22) Filed: Jan. 28, 2000

(65) Prior Publication Data

US 2003/0082185 A1 May 1, 2003

(51) Int. Cl.$^7$ .................. A61K 39/42; A61K 39/00; G01N 33/53
(52) U.S. Cl. ...................... 424/160.1; 424/208.1; 424/184.1; 424/185.1; 530/387.3; 435/7.1
(58) Field of Search ............. 424/160.1, 208.1, 424/184.1, 185.1; 530/387.3; 435/7.1

(56) References Cited

U.S. PATENT DOCUMENTS

| 5,464,933 | A | * | 11/1995 | Bolognesi et al. | .......... 530/324 |
| 5,603,933 | A | * | 2/1997 | Dwyer, IV et al. | ...... 424/185.1 |
| 5,668,149 | A | * | 9/1997 | Oroszlan et al. | ............ 514/313 |
| 5,817,767 | A | * | 10/1998 | Allaway et al. | ......... 530/387.3 |

FOREIGN PATENT DOCUMENTS

| WO | WO-9201451 A1 | * | 2/1992 |

OTHER PUBLICATIONS

Gait, M. J., et al., Progress in anti–HIV structure–based drug design, Trends in Biotechnology, vol. 13, No. 10, pp. 430–437, 1995.*
Allaway GP, et al., Expression and characterization of CD4–IgG2, a novel heterotetramer which neutralizes primary HIV–1 isolates. AIDS Research and Human Retroviruses 1995; 11:533–539. (Exhibit 1).
Allaway GP, et al.,. Synergistic inhibition of HIV–1 envelope–mediated cell fusion by CD4–based molecules in combination with antibodies to gp120 or gp41. AIDS Research & Human Retroviruses 1993; 9:581–587. (Exhibit 2).
Arthos J, et al., Identification of the residues in human CD4 critical for the binding of HIV. Cell 1989; 57:469–481. (Exhibit 3).
Burkly L, et al., Synergistic inhibition of human immunodeficiency virus type 1 envelope glycoprotein–mediated cell fusion and infection by an antibody to CD4 domain 2 in combination with anti–gp120 antibodies. Journal of Virology 1995; 69:4267–4273. (Exhibit 4).
Burton DR, et al., Efficient neutralization of primary isolates of HIV–1 by a recombinant human monoclonal antibody. Science 1994; 266:1024–1027. (Exhibit 5).
Capon DJ, et al., Designing CD4 immunoadhesins for AIDS therapy. Nature 1989; 337:525–531. (Exhibit 6).
Chan DC, et al., Evidence that a prominent cavity in the coiled coil of HIV type 1 gp41 is an attractive drug target. Proc Natl Acad Sci U S A 1998; 95:15613–15617. (Exhibit 7).
Clapham PR., et al., Soluble CD4 blocks the infectivity of diverse strains of HIV and SIV for T cells and monocytes but not for brain and muscle cells. Nature 1989; 337:368–370. (Exhibit 8).
Cushman M, et al., Preparation and anti–HIV activities of aurintricarboxylic acid fractions and analogues: direct correlation of antiviral potency with molecular weight. J Med Chem 1991; 34:329–337. (Exhibit 9).
Deen KC., et al., A soluble form of CD4 (T4) protein inhibits AIDS virus infection. Nature 1988; 331:82–84. (Exhibit 10).
Fouts TR, et al., Neutralization of the human immunodeficiency virus type 1 primary isolate JR–FL by human monoclonal antibodies correlates with antibody binding to the oligomeric form of the envelope glycoprotein complex. Journal of Virology 1997; 71:2779–2785. (Exhibit 11).
Gauduin M–C., et al., Effective ex vivo neutralization of plasma HIV–1 by recombinant immunoglobulin molecules. Journal of Virology 1996; 70:2586–2592. (Exhibit 12).
Jacobson J, et al., Results of a Rhase I Trial of Single–Dose PRO 542, a Novel Inhibitor of HIV Entry. Abstracts of the 39th Interscience Conference on Antimicrobial Agents and Chemotherapy 1999; 14. (Exhibit 13).

(List continued on next page.)

Primary Examiner—James Housel
Assistant Examiner—Stacy B. Chen
(74) Attorney, Agent, or Firm—John P. White; Cooper & Dunham LLP

(57) ABSTRACT

This invention provides a composition which comprises an admixture of two compounds, wherein one compound retards attachment of HIV-1 to a CD4+ cell by retarding binding of HIV-1 gp120 envelope glycoprotein to CD4 on the surface of the CD4+ cell and the other compound retards gp41 from adopting a conformation capable of mediating fusion of HIV-1 to a CD4+ cell by binding noncovalently to an epitope on a gp41 fusion intermediate, wherein the relative mass ratio of the compounds in the admixture ranges from about 100:1 to about 1:100, the composition being effective to inhibit HIV-1 infection of the CD4+ cell. This invention also provides a method of inhibiting HIV-1 infection of a CD4+ cell which comprises contacting the CD4+ cell with an amount of the above composition effective to inhibit HIV-1 infection of the CD4+ cell so as to thereby inhibit HIV-1 infection of the CD4+ cell.

15 Claims, 3 Drawing Sheets

OTHER PUBLICATIONS

Figure 1:
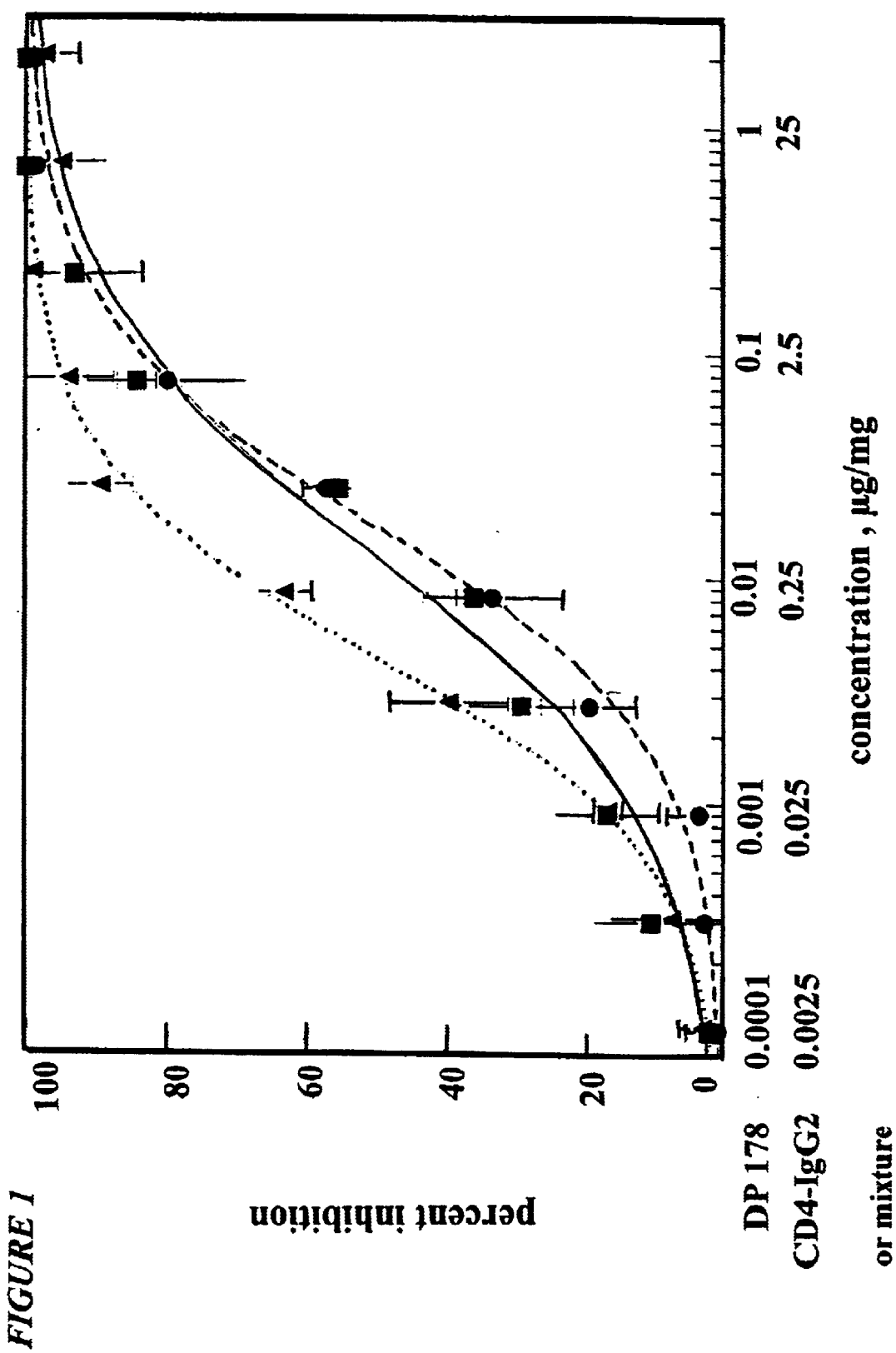

Ji H, Shu W, et al., Inhibition of human immunodeficiency virus type 1 infectivity by the gp41 core: role of a conserved hydrophobic cavity in membrane fusion. Journal of Virology 1999; 73:8578–8586. (Exhibit 14).

Jiang S, et al., HIV–1 inhibition by a peptide. Nature 1993; 365:113. (Exhibit 15).

Laal S, et al., Synergistic neutralization of human immunodeficiency virus type 1 by combinations of human monoclonal antibodies. Journal of Virology 1994; 68:4001–4008. (Exhibit 16).

LaCasse RA, et al., Fusion–competent vaccines: broad neutralization of primary isolates of HIV. Science 1999; 283:357–362. (Exhibit 17).

Li A, et al., Synergistic neutralization of a chimeric SIV/HIV type 1 virus with combinations of human anti–HIV type 1 envelope monoclonal antibodies or hyperimmune globulins. AIDS Res Hum Retroviruses 1997; 13:647–656. (Exhibit 18).

Li A, et al., Synergistic neutralization of simian–human immunodeficiency virus SHIV—vpu+ by triple and quadruple combinations of human monoclonal antibodies and high–titer anti–human immunodeficiency virus type 1 immunoglobulins. Journal of Virology 1998; 72:3235–3240. (Exhibit 19).

Litwin V, et al., Human immunodeficiency virus type 1 membrane fusion mediated by a laboratory–adapted strain and a primary isolate analyzed by resonance energy transfer. Journal of Virology 1996; 70:6437–6441. (Exhibit 20).

Mohan P, et al., Sulfonic acid polymers as a new class of human immunodeficiency virus inhibitors. Antiviral Res 1992; 18:139–150. (Exhibit 21).

Olson WC, et al., Differential inhibition of human immunodeficiency virus type 1 fusion, gp120 binding, and CC–chemokine activity by monoclonal antibodies to CCR5. J Virol 1999; 73:4145–4155. (Exhibit 22).

Posner MR., et al., Neutralization of HIV–1 by F105, a human monoclonal antibody to the CD4 binding site of gp120. Journal of Acquired Immune Deficiency Syndromes 1993; 6:7–14. (Exhibit 23).

Schols D, et al., Dextran sulfate and other polyanionic anti–HIV compounds specifically interact with the viral gp120 glycoprotein expressed by T–cells persistently infected with HIV–1. Virology 1990; 175:556–561. (Exhibit 24).

Schols, D, et al., Selective inhibitory activity of polyhydroxycarboxylates derived from phenolic compounds against human immunodeficiency virus replication. J Acquir Immune Defic Syndr 1991; 4:677–685. (Exhibit 25).

Thali M, et al., Cooperativity of neutralizing antibodies directed against the V3 and CD4 binding regions of the human immunodeficiency virus gp120 envelope glycoprotein. J Acquir Immune Defic Syndr 1992; 5:591–599. (Exhibit 26).

Tilley SA, et al., Synergistic neutralization of HIV–1 by human monoclonal antibodies against the V3 loop and the CD4–binding site of gp120. AIDS Res Hum Retroviruses 1992; 8:461–467. (Exhibit 27).

Trkola A, et al., Neutralization sensitivity of human immunodeficiency virus type 1 primary isolates to antibodies and CD4–based reagents is independent of coreceptor usage. J Virol 1998; 72:1876–1885. (Exhibit 28).

Vijh–Warrier S, et al., Synergistic neutralization of human immunodeficiency virus type 1 by a chimpanzee monoclonal antibody against the V2 domain of gp120 in combination with monoclonal antibodies against the V3 loop and the CD4– binding site. Journal of Virology 1996; 70:4466–4473 (Exhibit 29).

Vita C, et al., Rational engineering of a miniprotein that reproduces the core of the CD4 site interacting with HIV–1 envelope glycoprotein. Proc Natl Acad Sci U S A 1999; 96:13091–13096. (Exhibit 30).

Wild C, et al., A synthetic peptide from HIV–1 gp41 is a potent inhibitor of virus– mediated cell–cell fusion. AIDS Res Hum Retroviruses 1993; 9:1051–1053. (Exhibit 31).

Wild C, et al., The inhibitory activity of an HIV type 1 peptide correlates with its ability to interact with a leucine zipper structure. AIDS Res Hum Retroviruses 1995; 11:323–325. (Exhibit 32).

Wild C, et al., A synthetic peptide inhibitor of human immunodeficiency virus replication: correlation between solution structure and viral inhibition. Proc Natl Acad Sci U S A 1992; 89:10537–10541. (Exhibit 33).

Wild CT, et al., Peptides corresponding to a predictive alpha–helical domain of human immunodeficiency virus type 1 gp41 are potent inhibitors of virus infection. Proc Natl Acad Sci U S A 1994; 91:9770–9774. (Exhibit 34).

Eckert, D.M. et al. (1999) "Inhibiting HIV–1 Entry: Discovery Of D–peptide Inhibitors That Target The gp41 Coiled–coil Pocket", Cell, vol. 99, No. 1, pp. 103–115, (Exhibit 1).

Ferrer, M. et al. (1999) "Selection Of gp41–mediated HIV–1 Cell Entry Inhibitors From Biased Combinatorial Libraries Of Non–natural Binding Elements", Nature Structural Biology, vol. 6, No. 10, pp. 953–959, (Exhibit 2).

Kirby J.M. et al. (1998) "Potent Suppression Of HIV–1 Replication In Humans By T–20, A Peptide Inhibitor of gp41–mediated Virus Entry", Nature Medicine, vol. 4, pp. 1302–1307, (Exhibit 3).

Markosyan, R.M. et al. (2002) "The Mechanism Of Inhibition Of HIV–1 Env–mediated Cell–Cell Fusion By Recombinant Cores Of gp41 Ectodomain", Virology, vol. 302, No. 1, pp. 174–184, (Exhibit 4).

Nagashima, K.A. et al. (2001) "Human Immunodeficiency Virus Type 1 Entry Inhibitors PRO 542 And T–20 Are Potently Synergistic In Blocking Virus–Cell And Cell–Cell Fusion", Journal of Infections Diseases, vol. 183, No. 7, pp. 1121–1125, (Exhibit 5).

* cited by examiner

Figure 2

|  | Combination Index ||||
|---|---|---|---|---|
|  | CD4-IgG2:T-20 Mass Ratio ||||
| Percent Inhibition | 25:1 (low) | 25:1 (high) | 5:1 | 1:1 |
| 95 | 0.32 | 0.20 | 0.22 | 0.50 |
| 90 | 0.38 | 0.25 | 0.27 | 0.55 |
| 85 | 0.43 | 0.29 | 0.30 | 0.59 |
| 80 | 0.47 | 0.33 | 0.34 | 0.62 |
| 75 | 0.51 | 0.36 | 0.37 | 0.65 |
| 70 | 0.54 | 0.39 | 0.40 | 0.67 |
| 65 | 0.58 | 0.42 | 0.43 | 0.70 |
| 60 | 0.61 | 0.45 | 0.45 | 0.73 |
| 55 | 0.65 | 0.48 | 0.49 | 0.75 |
| 50 | 0.69 | 0.51 | 0.52 | 0.78 |

Figure 3

| Percent Inhibition | T-20 | | | CD4-IgG2 | | |
|---|---|---|---|---|---|---|
| | Concentration, μg/ml | | Dose Reduction | Concentration, μg/ml | | Dose Reduction |
| | Alone | Combination | | Alone | Combination | |
| 99 | 1.1 | 0.17 | 6.6 | 130 | 4.3 | 29 |
| 95 | 0.21 | 0.044 | 4.9 | 19 | 1.10 | 17 |
| 90 | 0.10 | 0.024 | 4.2 | 7.8 | 0.59 | 13 |
| 70 | 0.025 | 0.0076 | 3.3 | 1.6 | 0.19 | 8.4 |
| 50 | 0.011 | 0.0039 | 2.8 | 0.60 | 0.095 | 6.3 |

SEQUENCE LISTING

<160> NUMBER OF SEQ ID NOS: 5

<210> SEQ ID NO 1
<211> LENGTH: 36
<212> TYPE: PRT
<213> ORGANISM: Artificial Sequence

```
<220> FEATURE:
<223> OTHER INFORMATION: Description of Artificial Sequence:
      T20 peptide

<400> SEQUENCE: 1

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
             35

<210> SEQ ID NO 2
<211> LENGTH: 38
<212> TYPE: PRT
<213> ORGANISM: Artificial Sequence
<220> FEATURE:
<223> OTHER INFORMATION: Description of Artificial Sequence: DP107
      peptide

<400> SEQUENCE: 2

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala Val Glu
            20                  25                  30

Arg Tyr Leu Lys Asp Gln
             35

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: N34 peptide

<400> SEQUENCE: 3

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: C28 peptide

<400> SEQUENCE: 4

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys
            20                  25

<210> SEQ ID NO 5
<211> LENGTH: 68
<212> TYPE: PRT
<213> ORGANISM: Artificial Sequence
<220> FEATURE:
<223> OTHER INFORMATION: Description of Artificial Sequence: N34(L6)C28
      peptide

<400> SEQUENCE: 5
```

```
Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ser Gly Gly Arg Gly Gly Trp Met Glu Trp Asp Arg Glu Ile
        35              40                  45

Asn Asn Tyr Thr Ser Leu Ile His Ser Leu Ile Glu Glu Ser Gln Asn
    50                  55                  60

Gln Gln Glu Lys
65
```

COMPOSITIONS AND METHODS FOR INHIBITION OF HIV-1 INFECTION

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

Infection of cells by human immunodeficiency virus type 1 (HIV-1) is mediated by the viral envelope (env) glycoproteins gp120 and gp41, which are expressed as a noncovalent, oligomeric complex on the surface of virus and virally infected cells. HIV-1 entry into target cells proceeds at the cell surface through a cascade of events that include (1) binding of the viral surface glycoprotein gp120 to cell surface CD4, which is the primary receptor for HIV-1, (2) env binding to fusion coreceptors such as CCR5 and CXCR4, and (3) multiple conformational changes in gp41. During fusion, gp41 adopts transient conformations that include a prehairpin fusion intermediate that ultimately folds into a conformation capable of mediating fusion. These events culminate in fusion of the viral and cellular membranes and the subsequent introduction of the viral genome into the target cell. A similar sequence of molecular events is required for infection to spread via fusion of infected and uninfected cells. Each stage of the viral entry process can be targeted for therapeutic intervention. HIV-1 attachment can be inhibited both by agents that bind the viral envelope glycoproteins and by agents that bind human CD4. Notably, HIV-1 attachment can be inhibited by compounds that incorporate the gp120-binding domains of human CD4 and molecular mimics thereof [1–7]. Because this interaction between gp120 and CD4 is essential for virus infection, CD4-based molecules have the potential to target most if not all strains of HIV-1. In addition, viruses have limited ability to develop resistance to such molecules.

The determinants for gp120 binding map to the first extracellular domain (D1) on CD4 [1], and the amino acids critical for binding center on a loop comprising amino acids 36–47. Potent HIV-1 inhibitory activity has been reproduced in a 27-amino acid peptide that mimics this loop and surrounding structures [7].

A number of recombinant CD4-based molecules have been developed and tested for clinical activity in man. The first of these contained the four extracellular domains (D1–D4) of CD4 but lacked the transmembrane and intracellular regions. This molecule, termed soluble CD4 (sCD4), demonstrated excellent tolerability when administered to humans at doses ranging to 10 mg/kg [8,9]. Transient reductions in plasma levels of infectious HIV-1 were observed in certain patients treated with sCD4. The short half-life of sCD4 in humans (45 minutes following intravenous administration) was identified as one obstacle to using this agent for chronic therapy.

Second-generation CD4-based proteins were developed with increased serum half-life. These CD4-immunoglobulin fusion proteins comprised the D1D2 domains of CD4 genetically fused to the hinge CH2 and CH3 regions of human IgG molecules. These divalent proteins derive HIV-1 neutralizing capacity from their CD4 domains and Fc effector functions from the IgG molecule. A CD4-IgG1 fusion protein was shown to have excellent tolerability and improved pharmacokinetics in Phase I clinical testing [10]. The antiviral evaluations were inconclusive.

More recently, a third-generation tetravalent CD4-IgG2 fusion protein was developed that comprises the D1D2 domains of CD4 genetically fused to the heavy and light chain constant regions of human IgG2. This agent binds the HIV-1 envelope glycoprotein gp120 with nanomolar affinity [5] and may inhibit virus attachment both by receptor blockade and by detaching gp120 from the virion surface, thereby irreversibly inactivating the virus. In standard PBMC-based neutralization assays, CD4-IgG2 neutralized primary HIV-1 isolates derived from all major subtypes and outlier groups. The CD4-IgG2 concentrations required to achieve a 90% reduction in viral infectivity, the in vitro IC90, were approximately 15–20 $\mu$g/ml [11], concentrations that are readily achievable in vivo. CD4-IgG2 was similarly effective in neutralizing HIV-1 obtained directly from the plasma of seropositive donors in an ex vivo assay, indicating that this agent is active against the diverse viral quasispecies that are encountered clinically [12]. CD4-IgG2 also provided protection against infection by primary isolates in the hu-PBL-SCID mouse model of HIV-1 infection [13]. Recent analyses have demonstrated that CD4-IgG2's ability to neutralize primary viruses is independent of their coreceptor usage [14].

Compared with mono- or divalent CD4-based proteins, CD4-IgG2 has consistently demonstrated as much as 100-fold greater potency at inhibiting primary HIV-1 isolates [5,12,14,15]. The heightened potency may derive from CD4-IgG2's ability to bind virions with increased valency/avidity and its steric juxtaposition of two gp120 binding sites on each Fab-like arm of the immunoglobulin molecule. The larger Fab-like arms of CD4-IgG2 are also more likely to span HIV-1 envelope spikes on the virion. In a variety of preclinical models, CD4-IgG2's anti-HIV-1 activity has been shown to compare favorably with those of the rare human monoclonal antibodies that broadly and potently neutralize primary HIV-1 isolates [5,11,14,15]. In addition, CD4-IgG2 therapy is in principle less susceptible to the development of drug-resistant viruses than therapies employing anti-env monoclonal antibodies or portions of the highly mutable HIV-1 envelope glycoproteins. These properties suggest that CD4-IgG2 may have clinical utility as an agent that neutralizes cell-free virus before it has the opportunity to establish new rounds of infection. In addition to treatment, CD4-IgG2 may have utility in preventing infection resulting from occupational, perinatal or other exposure to HIV-1.

In Phase I clinical testing, single-dose CD4-IgG2 demonstrated excellent pharmacology and tolerability. In addition, measurable antiviral activity was observed by each of two measures. First, a statistically significant acute reduction in plasma HIV RNA was observed following administration of a single 10 mg/kg dose. In addition, sustained reductions in plasma levels of infectious HIV were observed in each of two patients tested. Taken together, these observations indicate that CD4-IgG2 possesses antiviral activity in humans [16].

In addition to CD4-based proteins and molecular mimics thereof, HIV-1 attachment can also be inhibited by antibodies and nonpeptidyl molecules. Known inhibitors include (1) anti-env antibodies such as IgG1b12 and F105 [17, 18], (2) anti-CD4 antibodies such as OKT4A, Leu 3a, and humanized versions thereof [19,20], and (3) nonpeptidyl agents that target either gp120 or CD4 [21], [22–24]. The latter group of compounds includes aurintricarboxylic acids, polyhydroxycarboxylates, sulfonic acid polymers, and dextran sulfates.

Several agents have been identified that block HIV-1 infection by targeting gp41 fusion intermediates. These inhibitors may interact with the fusion intermediates and prevent them from folding into final fusogenic conformations. The first such agents to be identified comprised synthetic or recombinant peptides corresponding to portions of the gp41 ectodomain predicted to form hydrophobic alpha helices. One such region is present in both the amino and carboxy segments of the extracellular portion of gp41, and recent crystallographic evidence suggests that these regions interact in the presumed fusogenic conformation of gp41 [25, 26]. HIV-1 infection can be inhibited by agents that bind to either N- or C-terminal gp41 epitopes that are exposed during fusion. These agents include the gp41-based peptides T-20 (formerly known as DP178), T-1249, DP107, N34, C28, and various fusion proteins and analogues thereof [27–33]. Other studies have identified inhibitors that comprise non-natural D-peptides and nonpeptidyl moieties [34, 35]. Clinical proof-of-concept for this class of inhibitors has been provided by T-20, which reduced plasma HIV RNA levels by as much as 2 logs in Phase I/II human clinical testing [36]. The broad antiviral activity demonstrated for this class of inhibitors reflects the high degree of gp41 sequence conservation amongst diverse strains of HIV-1.

Recent studies [37] have demonstrated the possibility of raising antibodies against HIV-1 fusion intermediates. This work employed "fusion-competent" HIV vaccine immunogens that capture transient fusion intermediates formed upon interaction of gp120/gp41 with CD4 and fusion coreceptors. The immunogens used in these studies were formalin-fixed cocultures of cells that express HIV-1 gp120/gp41 and cells that express human CD4 and CCR5 but not CXCR4. The antibodies elicited by the vaccines demonstrated unprecedented breadth and potency in inhibiting primary HIV-1 isolates regardless of their coreceptor usage, indicating that the antibodies were raised against structures such as gp41 fusion intermediates that are highly conserved and transiently exposed during HIV-1 entry. This class of antibodies does not include the anti-gp41 monoclonal antibody known as 2F5, which interacts with an epitope that is constitutively presented on virus particles prior to fusion [38].

Previously, synergistic inhibition of HIV-1 entry has been demonstrated using certain anti-env antibodies used in combination with other anti-env antibodies [39–44], anti-CD4 antibodies [45] or CD4-based proteins [6]. Similarly, synergies have been observed using anti-CCR5 antibodies used in combination with other anti-CCR5 antibodies, CC-chemokines, or CD4-based proteins [46]. However, no prior studies have examined the potential synergistic effects of combining inhibitors of gp41 fusion intermediates with inhibitors of other stages of HIV-1 entry. In particular, no studies have examined combinations of inhibitors of gp41 fusion intermediates and HIV-1 attachment.

SUMMARY OF THE INVENTION

This invention provides a composition which comprises an admixture of two compounds, wherein one compound retards attachment of HIV-1 to a CD4+ cell by retarding binding of HIV-1 gp120 envelope glycoprotein to CD4+ on the surface of the CD4+ cell and the other compound retards gp41 from adopting a conformation capable of mediating fusion of HIV-1 to a CD4+ cell by binding noncovalently to an epitope on a gp41 fusion intermediate, wherein the relative mass ratio of the compounds in the admixture ranges from about 100:1 to about 1:100, the composition being effective to inhibit HIV-1 infection of the CD4+ cell.

This invention provides a method of inhibiting HIV-1 infection of a CD4+ cell which comprises contacting the CD4+ cell with an amount of the above composition effective to inhibit HIV-1 infection of the CD4+ cell so as to thereby inhibit HIV-1 infection of the CD4+ cell.

This invention provides a method of inhibiting HIV-1 infection of a CD4+ cell which comprises contacting the CD4+ cell with an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell and an amount of a compound which retards gp41 from adopting a conformation capable of mediating fusion of HIV-1 to a CD4+ cell by binding noncovalently to an epitope on a gp41 fusion intermediate so as to thereby inhibit HIV-1 infection of the CD4+ cell.

BRIEF DESCRIPTION OF THE FIGURES

FIG. 1

Synergistic inhibition of HIV-1 entry CD4-IgG2 ( - - - ■ - - - ), T-20 ( - - - ● - - - ), and a 25:1 CD4-IgG2:T-20 combination ( . . . ▲ . . . ) were analyzed for inhibition of HIV-1 entry in an env-mediated membrane fusion (RET) assay. Inhibitors were added to a mix of HeLa-$Env_{JR-FL}{}^{+}$ and PM1 cells previously labeled with F18 and R18 respectively. Fluorescence RET was measured after 4 h of incubation, and percent inhibition was calculated as described [19]. Results are mean values from three independent experiments. The data were analyzed according to the median effect principle described in Equation (1). The best-fit parameters for K and m are 0.31 μg/ml and 0.73 for CD4-IgG2, 0.017 μg/ml and 0.92 for T-20, and 0.11 μg/ml and 1.0 for their combination. These curves are plotted and indicate a reasonable goodness-of-fit between experiment and theory ($r^2$=0.983, 0.998, and 0.996 for CD4-IgG2, T-20, and their combination, respectively). To normalize for the differences in potencies of the compounds, separate concentrations scales are used for CD4-IgG2 and the 25:1 CD4-IgG2: T-20 mixture and for T-20, as indicated.

FIG. 2

Combination indices for inhibition of HIV-1 entry by combinations of CD4-IgG2 and T-20. CD4-IgG2, T-20 and fixed mass ratios thereof were analyzed in the RET assay for the ability to inhibit env-mediated membrane fusion. The 25:1 (high) combination examined 10 three-fold serial dilutions of 250 μg/ml CD4-IgG2, 10 μg/ml T-20 and their combination. The 25:1 (low) combination examined 10 three-fold serial dilutions of 50 μg/ml CD4-IgG2, 2 μg/ml T-20 and their combination. The 5:1 combination examined 10 three-fold serial dilutions of 50 μg/ml CD4-IgG2, 2 μg/ml T-20, and their combination. The 1:1 combination examined 10 three-fold serial dilutions of 10 μg/ml CD4-IgG2, 10 μg/ml T-20 and their combination. Inhibition data from three or more independent assays were averaged prior to analysis. Dose-response curves for the various inhibitors and combinations were fit to Equation (1), which was then rearranged to calculate the inhibitor concentrations required to effect a given percent inhibition. The concentrations of the individual agents in an inhibitory mixture were calculated from their known mass ratios. These values were then used to calculate the Combination Index (CI) according to Equation (2). CI<1 indicates synergy, CI=1 indicates additive effects, and CI>1 indicates antagonism.

FIG. 3

Dose reductions observed for synergistic combinations of CD4-IgG2 and T-20. CD4-IgG2, T-20 and a 25:1 fixed mass ratio thereof were tested in the RET assay for the ability to inhibit env-mediated membrane fusion. Inhibition data from six independent assays were averaged. K and m were determined by curve-fitting the dose-response curves, and Equation (1) was rearranged to allow calculation of c for a given f for the single agents and their combination. Dose Reduction is the ratio of the inhibitor concentrations required to achieve a given degree of inhibition when the inhibitor is used alone v. in a synergistic combination.

DETAILED DESCRIPTION OF THE INVENTION

The plasmids CD4-IgG2-HC-pRcCMV and CD4-kLC-pRcCMV were deposited pursuant to, and in satisfaction of, the requirements of the Budapest Treaty on the International Recognition of the Deposit of Microorganisms (the "Budapest Treaty") for the Purposes of Patent Procedure with the American Type Culture Collection (ATCC), 12301 Parklawn Drive, Rockville, Md. 20852 under ATCC Accession Nos. 75193 and 75194, respectively. The plasmids were deposited with ATCC on Jan. 30, 1992. The plasmid designated pMA243 was similarly deposited in accordance with the Budapest Treaty with ATCC under Accession No. 75626 on Dec. 16, 1993.

As used herein, the following standard abbreviations are used throughout the specification to indicate specific amino acids:

| | |
|---|---|
| A = ala = alanine | R = arg = arginine |
| N = asn = asparagine | D = asp = aspartic acid |
| C = cys = cysteine | Q = gln = glutamine |
| E = glu = glutamic acid | G = gly = glycine |
| H = his = histidine | I = ile = isoleucine |
| L = leu = leucine | K = lys = lysine |
| M = met = methionine | F = phe = phenylalanine |
| P = pro = proline | S = ser = serine |
| T = thr = threonine | W = trp = tryptophan |
| Y = tyr = tyrosine | V = val = valine |

This invention provides a composition which comprises an admixture of two compounds, wherein one compound retards attachment of HIV-1 to a CD4+ cell by retarding binding of HIV-1 gp120 envelope glycoprotein to CD4 on the surface of the CD4+ cell and the other compound retards gp41 from adopting a conformation capable of mediating fusion of HIV-1 to a CD4+ cell by binding noncovalently to an epitope on a gp41 fusion intermediate, wherein the relative mass ratio of the compounds in the admixture ranges from about 100:1 to about 1:100, the composition being effective to inhibit HIV-1 infection of the CD4+ cell.

As used herein, "HIV-1" means the human immunodeficiency virus type-1. HIV-1 includes but is not limited to extracellular virus particles and the forms of HIV-1 associated with HIV-1 infected cells. HIV-$1_{JR-FL}$ is a strain that was originally isolated at autopsy from the brain tissue of an AIDS patient [47]. The virus was co-cultured with lectin-stimulated normal human peripheral blood mononuclear cells. The virus has been cloned and the DNA sequences of its envelope glycoproteins are known (Genbank Accession #U63632). In terms of sensitivity to inhibitors of viral entry, HIV-$1_{JR-FL}$ is known to be highly representative of primary HIV-1 isolates [11, 14, 15, 48–50].

As used herein, "gp41 fusion intermediates" includes structures, conformations, and oligomeric states that are preferentially and transiently presented or exposed on the HIV-1 envelope glycoprotein gp41 during the process of HIV-1 env-mediated membrane fusion. These intermediates may form upon interaction of HIV-1 with cellular receptors or may be present in partially or fully occluded states on HIV-1 prior to its interaction with cellular receptors. "gp41 fusion intermediates" do not include fusogenic gp41 conformations that cannot provide targets for therapeutic intervention.

The gp41 fusion intermediates may contain multiple epitopes that are transiently exposed during fusion and can provide targets for therapeutic intervention. As used herein, an "N-terminal gp41 epitope" may comprise all or portions of the sequences from amino acid A541 to Q590. As used herein, a "C-terminal gp41 epitope" may comprise all or portions of the sequences from amino acid W628 to L663. These epitopes have the potential to form coiled-coils of interacting alpha helical segments by virtue of heptad (sequence of seven amino acids) repeats containing hydrophobic amino acids at positions 1 and 4 of the heptad. The amino acid numbering system is for the H×B2 isolate of HIV-1 (Genbank Protein Accession No. AAB50262). Because of the sequence variability of HIV-1 envelope proteins, the composition, size and precise location of such sequences may be different for different viral isolates. The gp41 fusion intermediates may also present other linear or conformational epitopes that are transiently expressed during HIV-1 entry. An inhibitor may target multiple epitopes present on gp41 fusion intermediates. Alternatively, separate inhibitors may be used in combination to target one or more epitopes present on gp41 fusion intermediates.

As used herein, "fusogenic" means capable of mediating membrane fusion. As used herein, "HIV-1 fusion coreceptor" means a cellular receptor that mediates fusion between the target cell expressing the receptor and HIV-1 or an HIV-1 envelope glycoprotein$^{-}$ cell. HIV-1 fusion co-receptors include but are not limited to CCR5, CXCR4 and other chemokine receptors. As used herein, "fusion" means the joining or union of the lipid bilayer membranes found on mammalian cells or viruses such as HIV-1. This process is distinguished from the attachment of HIV-1 to a target cell. Attachment is mediated by the binding of the HIV-1 exterior glycoprotein to the human CD4 receptor, which is not a fusion co-receptor.

As used herein, "retards" means that the amount is reduced. As used herein, "attachment" means the process that is mediated by the binding of the HIV-1 envelope glycoprotein to the human CD4 receptor, which is not a fusion co-receptor. As used herein, "CD4" means the mature, native, membrane-bound CD4 protein comprising a cytoplasmic domain, a hydrophobic transmembrane domain, and an extracellular domain which binds to the HIV-1 gp120 envelope glycoprotein.

As used herein, "epitope" means a portion of a molecule or molecules that form a surface for binding antibodies or other compounds. The epitope may comprise contiguous or noncontiguous amino acids, carbohydrate or other nonpeptidyl moities or oligomer-specific surfaces.

The compounds of the subject invention have shown to demonstrate a synergistic effect. As used herein, "synergistic" means that the combined effect of the compounds when used in combination is greater than their additive effects when used individually.

In one embodiment of the above composition, the compound which retards attachment of HIV-1 to the CD4+ cell by retarding binding of HIV-1 gp120 envelope glycoprotein to CD4 on the surface of the CD4+ cell is a CD4-based protein. As used herein, "CD4-based protein" means any protein comprising at least one sequence of amino acid residues corresponding to that portion of CD4 which is required for CD4 to form a complex with the HIV-1 gp120 envelope glycoprotein.

In one embodiment, the CD4-based protein is a CD4-immunoglobulin fusion protein. In one embodiment, the CD4-immunoglobulin fusion protein is CD4-IgG2, which is a heterotetrameric CD4-human IgG2 fusion protein. In one embodiment, the CD4-IgG2 comprises two heavy chains and two lights chains, wherein the heavy chains are encoded by an expression vector designated CD4-IgG2HC-pRcCMV (ATCC Accession No. 75193) and the light chains are encoded by an expression vector designated CD4-kLC-pRcCMV (ATCC Accession No. 75194).

In one embodiment of the above composition, the compound which retards attachment of HIV-1 to the CD4+ cell by retarding binding of HIV-1 gp120 envelope glycoprotein to CD4 on the surface of the CD4+ cell is a protein, the amino acid sequence of which comprises that of a protein found in HIV-1 as an envelope glycoprotein. In one embodiment, the protein binds to an epitope of CD4 on the surface of the CD4+ cell. The envelope glycoprotein includes but is not limited to gp120, gp160, or gp140.

In one embodiment of the above composition, the compound which retards the attachment of HIV-1 to the CD4+ cell by retarding binding of HIV-1 gp120 envelope glycoprotein to CD4 on the surface of the CD4+ cell is an antibody or portion of an antibody. In one embodiment, the antibody is a monoclonal antibody. The antibody of the subject invention may be a human, humanized or chimeric antibody. In one embodiment, the portion of the antibody is a Fab fragment of the antibody. In one embodiment, the portion of the antibody comprises the variable domain of the antibody. In one embodiment, the portion of the antibody comprises a CDR portion of the antibody. The monoclonal antibody of the subject invention includes but is not limited to an IgG, IgM, IgD, IgA, or IgE monoclonal antibody.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man. Methods for humanizing antibodies are known to those skilled in the art.

In one embodiment, the monoclonal antibody binds to an HIV-1 envelope glycoprotein. The HIV-1 envelope glycoprotein includes but is not limited to gp120 and gp160.

In one embodiment, the HIV-1 envelope glycoprotein is gp120 and the monoclonal antibody which binds to gp120 is IgG1b12 or F105. IgG1b12 is listed as item #2640 in the NIH AIDS Research and Reference Reagent Program Catalog. F105 is listed as item #857 in the NIH AIDS Research and Reference Reagent Program Catalog.

In one embodiment, the antibody binds to an epitope of CD4 on the surface of the CD4+ cell.

In one embodiment, the compound which retards attachment of HIV-1 to the CD4+ cell by retarding binding of HIV-1 gp120 envelope glycoprotein to CD4 on the surface of the CD4+ cell is a peptide. In one embodiment, the compound which retards attachment of HIV-1 to the CD4+ cell is a nonpeptidyl agent. As used herein, "nonpeptidyl" means that the agent does not consist in its entirety of a linear sequence of amino acids linked by peptide bonds. A nonpeptidyl agent may, however, contain one or more peptide bonds.

In one embodiment of the above composition, the compound which retards gp41 from adopting a conformation capable of mediating fusion of HIV-1 to a CD4+ cell by binding noncovalently to an epitope on a gp41 fusion intermediate is an antibody.

In one embodiment, the antibody is a monoclonal antibody. In another embodiment, the antibody is a polyclonal antibody.

In one embodiment of the above composition, the compound which retards gp41 from adopting a conformation capable of mediating fusion of HIV-1 to a CD4+ cell by binding noncovalently to an epitope on a gp41 fusion intermediate is a peptide.

In one embodiment, the compound which retards gp41 from adopting a conformation capable of mediating fusion of HIV-1 to a CD4+ cell by binding noncovalently to an epitope on a gp41 fusion intermediate is a fusion protein which comprises a peptide selected from the group consisting of T-20 (SEQ ID NO: 1), DP107 (SEQ ID NO: 2), N34 (SEQ ID NO: 3), C28 (SEQ ID NO: 4), and N34(L6)C28 (SEQ ID NO: 5).

```
As used herein, "T-20" and "DP178" are used
interchangeably to denote a peptide having the
following amino acid sequence:
YTSLIHSLIEESQNQQEKNEQELLELDKWASLWNWF  (SEQ ID NO:1)
and as described [29,32].

DP107 has the following amino acid sequence:
NNLLRAIEAQQHLLQLTVWGIKQLQARILAVERYLKD (SEQ ID NO:2)
Q N34 has the following amino acid sequence:
SGIVQQQNNLLRAIEAQQHLLQLTVWGIKQLQAR    (SEQ ID NO:3)

C28 has the following amino acid sequence:
WMEWDREINNYTSLIHSLIEESQNQQEK          (SEQ ID NO:4)

N34 (L6) C28 has the following amino acid
sequence:
SGIVQQQNNLLRAIEAQQHLLQLTVWGIKQLQARSGG (SEQ ID NO:5)
RGGWMEWDREINNYTSLIHSLIEESQNQQEK
```

In one embodiment of the above composition, the peptide is selected from the group consisting of T-20 (SEQ ID NO: 1), DP107 (SEQ ID NO: 2), N34 (SEQ ID NO: 3), C28 (SEQ ID NO: 4), and N34(L6)C28 (SEQ ID NO: 5).

In one embodiment of the above composition, the peptide is T-20 (SEQ ID NO: 1).

In one embodiment of the above composition, the peptide is a mutant peptide which (1) consists of amino acids having a sequence identical to that of a wildtype peptide selected from the group consisting of T-20 (SEQ ID NO: 1), DP-107 (SEQ ID NO: 2), N34 (SEQ ID NO: 3), C28 (SEQ ID NO: 4), and N34(L6)C28 (SEQ ID NO: 5), except for an addition of at least one glycine residue to a 5' end of the peptide, to a 3' end of the peptide, or to both ends of the peptide and (2) retards gp41 from adopting a conformation capable of mediating fusion of HIV-1 to a CD4+ cell by binding noncovalently to an epitope on a gp41 fusion intermediate.

In one embodiment, the compound which retards gp41 from adopting a conformation capable of mediating fusion of HIV-1 to a CD4+ cell by binding noncovalently to an epitope on a gp41 fusion intermediate is a non-peptidyl agent.

In one embodiment of the above composition, the relative mass ratio of each such compound in the admixture ranges from about 25:1 to about 1:1.

In one embodiment of the above composition, the mass ratio is about 25:1

In one embodiment of the above composition, the mass ratio is about 5:1.

In one embodiment of the above composition, the mass ratio is about 1:1.

In one embodiment of the above composition, the composition is admixed with a carrier. The carrier of the subject invention may be an aerosol, intravenous, oral or topical carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a method of inhibiting HIV-1 infection of a CD4+ cell which comprises contacting the CD4+ cell with an amount of the above composition effective to inhibit HIV-1 infection of the CD4+ cell so as to thereby inhibit HIV-1 infection of the CD4+ cell.

In one embodiment, the CD4+ cell is present in a subject and the contacting is effected by administering the composition to the subject.

As used herein, "subject" includes any animal or artificially modified animal capable of becoming HIV-infected. Artificially modified animals include, but are not limited to, SCID mice with human immune systems. The animals include but are not limited to mice, rats, dogs, cats, guinea pigs, ferrets, rabbits, and primates. In the preferred embodiment, the subject is a human.

In one embodiment, the effective amount of the composition comprises from about 0.000001 mg/kg body weight to about 100 mg/kg body weight of the subject.

As used herein, "administering" may be effected or performed using any of the methods known to one skilled in the art, which includes intralesional, intraperitoneal, intramuscular, subcutaneous, intravenous, liposome mediated delivery, transmucosal, intestinal, topical, nasal, oral, anal, ocular or otic delivery. The compounds may be administered separately (e.g., by different routes of administration, sites of injection, or dosing schedules) so as to combine in synergistically effective amounts in the subject.

The dose of the composition of the invention will vary depending on the subject and upon the particular route of administration used. Dosages can range from 0.1 to 100,000 $\mu$g/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming infected with HIV-1. A person of ordinary skill in the art can perform simple titration experiments to determine what amount is required to treat the subject.

This invention provides a method of inhibiting HIV-1 infection of a CD4+ cell which comprises contacting the CD4+ cell with an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell and an amount of a compound which retards gp41 from adopting a conformation capable of mediating fusion of HIV-1 to a CD4+ cell by binding noncovalently to an epitope on a gp41 fusion intermediate so as to thereby inhibit HIV-1 infection of the CD4+ cell.

In one embodiment, the CD4+ cell is present in a subject and the contacting is effected by administering the compounds to the subject.

In one embodiment, the compounds are administered to the subject simultaneously. In another embodiment, the compounds are administered to the subject at different times. In one embodiment, the compounds are administered to the subject by different routes of administration.

The subject invention has various applications which includes HIV treatment such as treating a subject who has become afflicted with HIV. As used herein, "afflicted with HIV-1" means that the subject has at least one cell which has been infected by HIV-1. As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV-1. Another application of the subject invention is to prevent a subject from contracting HIV. As used herein, "contracting HIV-1" means becoming infected with HIV-1, whose genetic information replicates in and/or incorporates into the host cells. Another application of the subject invention is to treat a subject who has become infected with HIV-1. As used herein, "HIV-1 infection" means the introduction of HIV-1 genetic information into a target cell, such as by fusion of the target cell membrane with HIV-1 or an HIV-1 envelope glycoprotein cell. The target cell may be a bodily cell of a subject. In the preferred embodiment, the target cell is a bodily cell from a human subject. Another application of the subject invention is to inhibit HIV-1 infection. As used herein, "inhibiting HIV-1 infection" means reducing the amount of HIV-1 genetic information introduced into a target cell population as compared to the amount that would be introduced without said composition.

This invention will be better understood from the Experimental Details that follow. However, one skilled in the art will readily appreciate that the specific methods and results discussed are merely illustrative of the invention as described more fully in the claims that follow thereafter.

Experimental Details

A. Materials and Methods

1) Reagents

Purified recombinant CD4-IgG2 protein was produced by Progenics Pharmaceuticals, Inc. from plasmids CD4-IgG2-HC-pRcCMV and CD4-kLC-pRcCMV (ATCC Accession Nos. 75193 and 75194, respectively) as described [5]. HeLa-env cells were prepared by transfecting HeLa cells (ATCC Catalog # CCL-2) with HIV-1 gp120/gp41 env-expressing plasmid pMA243 as described [51]. PM1 cells are available from the National Institutes of Health AIDS Reagent Program (Catalog #3038). The T-20 peptide was synthesized using standard solid-chase Fmoc chemistry and purified and characterized as described [31, 32].

2) Inhibition of HIV-1 Env-mediated Membrane Fusion

HIV-1 envelope-mediated fusion between HeLa-Env$_{JR-FL}$ and PM1 cells was detected using a Resonance Energy Transfer (RET) assay. Equal numbers (2×104) of fluorescein octadecyl ester (F18)-labeled envelope-expressing cells and octadecyl rhodamine (R18)-labeled PM1 cells were plated in 96-well plates in 15% fetal calf serum in phosphate buffered saline and incubated for 4 h at 37 (C in the presence of varying concentrations of CD4-IgG2, T-20 or combinations thereof. Fluorescence RET was measured with a Cytofluor plate-reader (PerSeptive Biosystems) and % RET was determined as previously described [19].

3) Quantitative Analysis of the Synergistic, Additive or Antagonistic Effects of Combining the Agents HIV-1 inhibition data were analyzed according to the Combination Index method of Chou and Talay [52,53]. The data are modeled according to the median-effect principle, which can be written $$f=1/[1+(K/c)^m] \quad (1)$$

where f is the fraction affected/inhibited, c is concentration, K is the concentration of agent required to produce the median effect, and m is an empirical coefficient describing the shape of the dose-response curve. Equation (1) is a generalized form of the equations describing Michaelis-Menton enzyme kinetics, Langmuir adsorption isotherms, and Henderson-Hasselbalch ionization equilibria, for which m=1 in all cases. In the present case, K is equal to the IC$_{50}$ value. K and m are determined by curve-fitting the dose-response curves.

After the best-fit parameters for K and m are obtained for the experimental agents and their combination, Equation (1) is rearranged to allow for calculation of c for a given f. The resulting table of values (e.g., Figure X) is used to calculate the Combination Index (CI) using the equation $$CI=c_{1m}/c_1+c_{2m}/c_2+c_{1m}c_{2m}/c_1C_2 \quad (2)$$

where $c_1$=concentration of compound 1 when used alone
$c_2$=concentration of compound 2 when used alone
$c_{1m}$=concentration of compound 1 in the mixture
$c_{2m}$=concentration of compound 2 in the mixture All concentrations are those required to achieve a given degree of inhibition. Equation (2) is used when the molecules are mutually nonexclusive, i.e., have different sites of action. Since this is the likely scenario for inhibitors of HIV-1 attachment and gp41 fusion intermediates, Equation (2) was used for all Combination Index calculations. Mutually nonexclusive calculations provide a more conservative estimate of the degree of synergy that mutually exclusive calculations, for which the $c_{1m}c_{2m}/c_1c_2$ term is dropped. CI<1 indicates synergy, CI=1 indicates purely additive effects, and CI>1 indicates antagonism. In general, CI values are most relevant at the higher levels of inhibition that are required to achieve a measurable clinical benefit.

B. Results and Discussion

Combinations of inhibitors of HIV-1 attachment and gp41 fusion intermediates were first tested for the ability to inhibit HIV-1 env-mediated membrane fusion in the RET assay. This assay has proven to be a highly successful model of the HIV-1 entry process. In this assay, env-dependent coreceptor usage patterns and cellular tropisms of the parental viruses are accurately reproduced [19]. Indeed, the assay was instrumental in demonstrating that CCR5 functions as a requisite fusion coreceptor and acts at the level of viral entry [54]. The fusion assay and infectious virus are similarly sensitive to inhibition by metal chelators and agents that target the full complement of viral and cellular receptors [19, 46, 55].

Dose-response curves were obtained for the agents used individually and in combination in both assays. Data were analyzed using the median effect principle [52, 53]. The concentrations of single-agents or their mixtures required to produce a given effect were quantitatively compared in a term known as the Combination Index (CI). CI>1 indicates antagonism, CI=1 indicates a purely additive effect, and CI<1 indicates a synergistic effect wherein the presence of one agent enhances the effect of another.

Combinations of CD4-IgG2 and T-20 were observed to be potently synergistic in inhibiting env-mediated membrane fusion. FIG. 1 illustrates representative dose-response curves obtained in the membrane fusion assay for CD4-IgG2, T-20, and combinations of the two. The curve for the combination is highly displaced towards lower inhibitor concentrations and provides qualitative evidence that CD4-IgG2 and T-20 act in a synergistic manner.

To quantitatively calculate the degree of synergy observed between CD4-IgG2 and T-20, we analyzed the dose-response curves according to the Combination Index method [52, 53]. The analysis included data obtained at 25:1, 5:1, and 1:1 CD4-IgG2:T-20 mass ratios. At the 25:1 mass ratio, both high (0–250 µg/ml CD4-IgG2 and 0–10 µg/ml T-20) and low (0–50 µg/ml CD4-IgG2 and 0–2 µg/ml T-20) concentration ranges were evaluated. As indicated in FIG. 2, potent synergies were observed over these broad ranges of inhibitor ratios and concentrations, with CI values as low as 0.20 under optimal conditions. This degree of synergy is remarkable since CI values of 0.2 are rarely observed for combinations involving anti-HIV-1 antibodies [41–44], reverse transcriptase inhibitors [56], or protease inhibitors [57]. The observed synergies indicate that HIV-1 attachment and formation of gp41 fusion intermediates are interdependent steps. One possibility is that attachment inhibitors, when used at suboptimal concentrations, may slow but not abrogate the binding of gp120 to CD4. In this case, gp41 fusion intermediates may be formed and persist on the virus (or infected cell) for longer periods of time at levels below that required for membrane fusion and thus provide better targets for inhibitory agents.

The observed synergies translate into significant reductions in the amounts of CD4-IgG2 and T-20 needed for inhibition. These reductions are illustrated in FIG. 3 for CD4-IgG2 and T-20 used in a 25:1 mass ratio. By way of example, inhibition of viral entry by 95% requires 0.21 µg/ml of T-20 used alone, 19 µg/ml of CD4-IgG2 used alone and 1.14 µg/ml of a combination containing 0.044 µg/ml of T-20 and 1.1 µg/ml of CD4-IgG2. The combination reduces the respective doses of T-20 and CD4-IgG2 by 5- and 17-fold, respectively. Still greater dose reductions are observed at higher levels of inhibition.

REFERENCES

1. Arthos J, Deen K C, Chaikin M A et al. Identification of the residues in human CD4 critical for the binding of HIV. Cell 1989; 57:469–481.
2. Clapham P R., Weber J N., Whitby D. et al. Soluble CD4 blocks the infectivity of diverse strains of HIV and SIV for T cells and monocytes but not for brain and muscle cells. Nature 1989; 337:368–370.
3. Deen K C., McDougal J S., Inacker R. et al. A soluble form of CD4 (T4) protein inhibits AIDS virus infection. Nature 1988; 331:82–84.
4. Capon D J, Chamow S M, Mordenti J et al. Designing CD4 immunoadhesins for AIDS therapy. Nature 1989; 337:525–531.
5. Allaway G P, Davis-Bruno K L, Beaudry G A et al. Expression and characterization of CD4-IgG2, a novel heterotetramer which neutralizes primary HIV-1 isolates. AIDS Research and Human Retroviruses 1995; 11:533–539.
6. Allaway G P, Ryder A M, Beaudry G A, Maddon P J. Synergistic inhibition of HIV-1 envelope-mediated cell fusion by CD4-based molecules in combination with antibodies to gp120 or gp41. AIDS Research & Human Retroviruses 1993; 9:581–587.
7. Vita C, Drakopoulou E, Vizzavona J et al. Rational engineering of a miniprotein that reproduces the core of the CD4 site interacting with HIV-1 envelope glycoprotein. Proc Natl Acad Sci USA 1999; 96:13091–13096.
8. Schacker T., Coombs R W., Collier A C. et al. The effects of high-dose recombinant soluble CD4 on human immunodeficiency virus type 1 viremia. Journal of Infectious Diseases 1994; 169:37–40.
9. Schacker T, Collier A C, Coombs R et al. Phase I study of high-dose, intravenous rsCD4 in subjects with advanced HIV-1 infection. J Acquir Immune Defic Syndr Hum Retrovirol 1995; 9:145–152.
10. Collier A C, Coombs R W, Katzenstein D et al. Safety, pharmacokinetics, and antiviral response of CD4-immunoglobulin G by intravenous bolus in AIDS and AIDS-related complex. J Acquir Immune Defic Syndr Hum Retrovirol 1995; 10:150–156.
11. Trkola A., Pomales A P., Yuan H. et al. Cross-clade neutralization of primary isolates of human immunodeficiency virus type 1 by human monoclonal antibodies and tetrameric CD4-IgG2. Journal of Virology 1995; 69:6609–6617.
12. Gauduin M -C., Allaway G P., Maddon P J., Barbas C F 3, Burton D R, Koup R A. Effective ex vivo neutralization of plasma HIV-1 by recombinant immunoglobulin molecules. Journal of Virology 1996; 70:2586–2592.
13. Gauduin M -C., Allaway G P, Olson W C, Weir R., Maddon P J, Koup R A. CD4-immunoglobulin G2 protects Hu-PBL-SCID mice against challenge by primary human immunodeficiency virus type 1 isolates. Journal of Virology 1998; 72:3475–3478.
14. Trkola A, Ketas T, KewalRamani V N et al. Neutralization sensitivity of human immunodeficiency virus type 1 primary isolates to antibodies and CD4-based reagents is independent of coreceptor usage. J Virol 1998; 72:1876–1885.
15. Fouts T R, Binley J M, Trkola A, Robinson J E, Moore J P. Neutralization of the human immunodeficiency virus type 1 primary isolate JR-FL by human monoclonal antibodies correlates with antibody binding to the oligomeric form of the envelope glycoprotein complex. Journal of Virology 1997; 71:2779–2785.
16. Jacobson J, Lowy I, Trkola A et al. Results of a Rhase I Trial of Single-Dose PRO 542, a Novel Inhibitor of HIV Entry. Abstracts of the 39th Interscience Conference on Antimicrobial Agents and Chemotherapy 1999; 14.
17. Burton D R, Pyati J, Koduri R et al. Efficient neutralization of primary isolates of HIV-1 by a recombinant human monoclonal antibody. Science 1994; 266:1024–1027.
18. Posner M R., Cavacini L A., Emes C L., Power J., Byrn R. Neutralization of HIV-1 by F105, a human monoclonal antibody to the CD4 binding site of gp120. Journal of Acquired Immune Deficiency Syndromes 1993; 6:7–14.
19. Litwin V, Nagashima K A, Ryder A M et al. Human immunodeficiency virus type I membrane fusion mediated by a laboratory-adapted strain and a primary isolate analyzed by resonance energy transfer. Journal of Virology 1996; 70:6437–6441.
20. Poignard P, Peng T, Sabbe R, Newman W, Mosier D E, Burton D R. Blocking of HIV-1 Co-receptor CCR5 in the hu-PBL-SCID Mouse Leads to a Co-receptor Switch. 6th Conference on Retroviruses and Opportunistic Infections 1999;
21. Cushman M, Wang P L, Chang S H et al. Preparation and anti-HIV activities of aurintricarboxylic acid fractions and analogues: direct correlation of antiviral potency with molecular weight. J Med Chem 1991; 34:329–337.
22. Mohan P, Schols D, Baba M, De Clercq E. Sulfonic acid polymers as a new class of human immunodeficiency virus inhibitors. Antiviral Res 1992; 18:139–150.
23. Schols D, Pauwels R, Desmyter J, De Clercq E. Dextran sulfate and other polyanionic anti-HIV compounds specifically interact with the viral gp120 glycoprotein expressed by T-cells persistently infected with HIV-1. Virology 1990; 175:556–561.
24. Schols D, Wutzler P, Klocking R, Heibig B, De Clercq E. Selective inhibitory activity of polyhydroxycarboxylates derived from phenolic compounds against human immunodeficiency virus replication. J Acquir Immune Defic Syndr 1991; 4:677–685.
25. Weissenhorn W, Dessen A, Harrison S C, Skehel J J, Wiley D C. Atomic structure of the ectodomain from HIV-1 gp41. Nature 1997; 387:426–430.
26. Chan D C, Fass D, Berger J M, Kim P S. Core Structure of gp41 from the HIV Envelope Glycoprotein. Cell 1997; 89:263–273.
27. Ji H, Shu W, Burling F T, Jiang S, Lu M. Inhibition of human immunodeficiency virus type 1 infectivity by the gp41 core: role of a conserved hydrophobic cavity in membrane fusion. Journal of Virology 1999; 73:8578–8586.
28. Jiang S, Lin K, Strick N, Neurath A R. HIV-1 inhibition by a peptide. Nature 1993; 365:113.
29. Wild C, Greenwell T, Matthews T. A synthetic peptide from HIV-1 gp41 is a potent inhibitor of virus-mediated cell—cell fusion. AIDS Res Hum Retroviruses 1993; 9:1051–1053.
30. Wild C, Greenwell T, Shugars D, Rimsky-Clarke L, Matthews T. The inhibitory activity of an HIV type 1 peptide correlates with its ability to interact with a leucine zipper structure. AIDS Res Hum Retroviruses 1995; 11:323–325.
31. Wild C, Oas T, McDanal C, Bolognesi D, Matthews T. A synthetic peptide inhibitor of human immunodeficiency virus replication: correlation between solution structure and viral inhibition. Proc Natl Acad Sci USA 1992; 89:10537–10541.
32. Wild C T, Shugars D C, Greenwell T K, McDanal C B, Matthews T J. Peptides corresponding to a predictive alpha-helical domain of human immunodeficiency virus type 1 gp41 are potent inhibitors of virus infection. Proc Natl Acad Sci USA 1994; 91:9770–9774.
33. Chan D C, Chutkowski C T, Kim P S. Evidence that a prominent cavity in the coiled coil of HIV type 1 gp41 is an attractive drug target. Proc Natl Acad Sci USA 1998; 95:15613–15617.

34. Ferrer M, Kapoor T M, Strassmaier T et al. Selection of gp41-mediated HIV-1 cell entry inhibitors from biased combinatorial libraries of non-natural binding elements. Nat Struct Biol 1999; 6:953–960.
35. Eckert D M, Malashkevich V N, Hong L H, Carr P A, Kim P S. Inhibiting HIV-1 entry: discovery of D-peptide inhibitors that target the gp41 coiled-coil pocket. Cell 1999; 99:103–115.
36. Kilby J M, Hopkins S, Venetta T M et al. Potent suppression of HIV-1 replication in humans by T-20, a peptide inhibitor of gp41-mediated virus entry. Nat Med 1998; 4:1302–1307.
37. LaCasse R A, Follis K E, Trahey M, Scarborough J D, Littman D R, Nunberg J H. Fusion-competent vaccines: broad neutralization of primary isolates of HIV. Science 1999; 283:357–362.
38. Neurath A R, Strick N, Lin K, Jiang S. Multifaceted consequences of anti-gp41 monoclonal antibody 2F5 binding to HIV type 1 virions. AIDS Res Hum Retroviruses 1995; 11:687–696.
39. Thali M, Furman C, Wahren 3 et al. Cooperativity of neutralizing antibodies directed against the V3 and CD4 binding regions of the human immunodeficiency virus gp120 envelope glycoprotein. J Acquir Immune Defic Syndr 1992; 5:591–599.
40. Tilley S A, Honnen W J, Racho M E, Chou T C, Pinter A. Synergistic neutralization of HIV-1 by human monoclonal antibodies against the V3 loop and the CD4-binding site of gp120. AIDS Res Hum Retroviruses 1992; 8:461–467.
41. Laal S, Burda S, Gorny M K, Karwowska S, Buchbinder A, Zolla-Pazner S. Synergistic neutralization of human immunodeficiency virus type 1 by combinations of human monoclonal antibodies. Journal of Virology 1994; 68:4001–4008.
42. Vijh-Warrier S, Pinter A, Honnen W J, Tilley S A. Synergistic neutralization of human immunodeficiency virus type 1 by a chimpanzee monoclonal antibody against the V2 domain of gp120 in combination with monoclonal antibodies against the V3 loop and the CD4-binding site. Journal of Virology 1996; 70:4466–4473.
43. Li A, Baba T W, Sodroski J et al. Synergistic neutralization of a chimeric SIV/HIV type 1 virus with combinations of human anti-HIV type 1 envelope monoclonal antibodies or hyperimmune globulins. AIDS Res Hum Retroviruses 1997; 13:647–656.
44. Li A, Katinger H, Posner M R et al. Synergistic neutralization of simian-human immunodeficiency virus SHIV- vpu+ by triple and quadruple combinations of human monoclonal antibodies and high-titer anti-human immunodeficiency virus type 1 immunoglobulins. Journal of Virology 1998; 72:3235–3240.
45. Burkly L, Mulrey N, Blumenthal R, Dimitrov D S. Synergistic inhibition of human immunodeficiency virus type 1 envelope glycoprotein-mediated cell fusion and infection by an antibody to CD4 domain 2 in combination with anti-gp120 antibodies. Journal of Virology 1995; 69:4267–4273.
46. Olson W C, Rabut G E, Nagashima K A et al. Differential inhibition of human immunodeficiency virus type 1 fusion, gp120 binding, and CC-chemokine activity by monoclonal antibodies to CCR5. J Virol 1999; 73:4145–4155.
47. O'Brien W A., Koyanagi Y., Namazie A. et al. HIV-1 tropism for mononuclear phagocytes can be determined by regions of gp120 outside the CD4-binding domain. Nature 1990; 348:69–73.
48. Trkola A, Matthews J, Gordon C, Ketas T, Moore J P. A cell line-based neutralization assay for primary human immunodeficiency virus type 1 isolates that use either the CCR5 or the CXCR4 coreceptor. J Virol 1999; 73:8966–8974.
49. Fouts T R, Trkola A, Fung M S, Moore J P. Interactions of polyclonal and monoclonal anti-glycoprotein 120 antibodies with oligomeric glycoprotein 120-glycoprotein 41 complexes of a primary HIV type 1 isolate: relationship to neutralization. AIDS Res Hum Retroviruses 1998; 14:591–597.
50. Dreyer K, Kallas E G, Planelles V, Montefiori D, McDermott M P, Hasan M S. Primary isolate neutralization by HIV type 1-infected patient sera in the era of highly active antiretroviral therapy. AIDS Research and Human Retroviruses 1999; 15:1563–1571.
51. Allaway G P, Litwin V M, Maddon P J. Progenics Pharmaceuticals, Inc. Methods for using resonance energy transfer-based assay of HIV-1 envelope glycoprotein-mediated membrane fusion, and kits for practicing same. International Filing Date Jun. 7, 1996. International Patent Application No. PCT/US96/09894. 1996;
52. Chou T C. The median effect principle and the combination index for quantitation of synergism and antagonism. Synergism and Antagonism in Chemotherapy 1991; 61–102.
53. Chou T C, Talalay P. Quantitative analysis of dose-effect relationships: the combined effects of multiple drugs or enzyme inhibitors. Advances in Enzyme Regulation 1984; 22:27–55.
54. Dragic T., Litwin V., Allaway G P. et al. HIV-1 entry into CD4+ cells is mediated by the chemokine receptor CC-CKR-5. Nature 1996; 381:667.
55. Donzella G A, Schols D, Lin S W et al. AMD3100, a small molecule inhibitor of HIV-1 entry via the CXCR4 co-receptor. Nature Medicine 1998; 4:72–77.
56. Johnson V A, Merrill D P, Videler J A et al. Two-drug combinations of zidovudine, didanosine, and recombinant interferon-alpha A inhibit replication of zidovudine-resistant human immunodeficiency virus type 1 synergistically in vitro. Journal of Infectious Diseases 1991; 164:646–655.
57. Merrill D P, Manion D J, Chou T C, Hirsch M S. Antagonism between human immunodeficiency virus type 1 protease inhibitors indinavir and saquinavir in vitro. Journal of Infectious Diseases 1997; 176:265–268.

What is claimed:

1. A composition which comprises an admixture of two compounds, wherein: (a) one compound is a CD4-IgG2 fusion protein comprising two heavy chains and two light chains, which heavy chains are encoded by an expression vector designated CD4-IgG2HC-pRcCMV (ATCC Accession No. 75193), and which light chains are encoded by an expression vector designated CD4-kLC-pRcCMV (ATCC Accession No. 75194), which compound retards attachment of HTV-1 to a CD4+ cell by retarding binding of HIV-1 gp120 envelope glycoprotein to CD4 on the surface of the CD4+ cell; and (b) the other compound is a peptide which retards gp41 from adopting a conformation capable of mediating fusion of HIV-1 to a CD4+ cell by binding noncovalently to an epitope on a gp41 fusion intermediate, wherein the peptide that retards gp41 comprises a portion of the gp41 extracellular domain, and wherein the relative mass ratio of the compounds in the admixture ranges from about 100:1 to about 1:100, the composition being effective to inhibit HIV-1 infection of the CD4+ cell.

2. The composition of claim 1, wherein the peptide which retards gp41 from adopting a conformation capable of mediating fusion of HIV-1 to a CD4+ cell by binding noncovalently to an epitope on a gp41 fusion intermediate selected from the group consisting of T-20 (SEQ ID NO: 1), DP107 (SEQ ID NO: 2), N34 (SEQ ID NO: 3), C28 (SEQ ID NO: 4), and N34(L6)C28 (SEQ ID NO: 5).

3. The composition of claim 1, wherein the peptide which retards gp41 from adopting a conformation capable of mediating fusion of HIV-1 to a CD4+ cell by binding noncovalently to an epitope on a gp41 fusion intermediate is T-20 (SEQ ID NO: 1).

4. The composition of claim 1, wherein the relative mass ratio of each such compound in the admixture ranges from about 25:1 to about 1:1.

5. The composition of claim 4, wherein the mass ratio is about 25:1.

6. The composition of claim 4, wherein the mass ratio is about 5:1.

7. The composition of claim 4, wherein the mass ratio is about 1:1.

8. The composition of claim 1, wherein the composition is admixed with a carrier.

9. A method of inhibiting HIV-1 infection of a CD4+ cell which comprises contacting the CD4+ cell with an amount of a composition, which composition comprises an admixture of two compounds, wherein: (a) one compound is a CD4-IgG2 fusion protein comprising two heavy chains and two light chains, which heavy chains are encoded by an expression vector designated CD4-IgG2HC-pRcCMV (ATCC Accession No. 75193), and which light chains are encoded by an expression vector designated CD4-kLC-pRcCMV (ATCC Accession No. 75194), which compound retards attachment of HIV-1 to a CD4+ cell by retarding binding of HIV-1 gp120 envelope glycoprotein to CD4 on the surface of the CD4+ cell; and (b) the other compound is a peptide which retards gp41 from adopting a confirmation capable of mediating fusion of HIV-1 to a CD4+ cell by binding noncovalently to an epitope on a gp41 fusion intermediate, wherein the peptide that retards gp41 comprises a portion of the gp41 extracellular domain, and wherein the relative mass ratio of the compounds in the admixture ranges from about 100:1 to about 1:100, which amount is effective to inhibit HIV-1 infection of the CD4+ cell, so as to thereby inhibit HIV-1 infection of the CD4+ cell.

10. The method of claim 9, wherein the CD4+ cell is present in a subject and the contacting is effected by administering the composition to the subject.

11. A method of inhibiting HIV-1 infection of a CD4+ cell which comprises contacting the CD4+ cell with: (a) an amount of a CD4-IgG2 fusion protein comprising two heavy chains and two light chains, which heavy chains are encoded by an expression vector designated CD4-IgG2HC-pRcCMV (ATCC Accession No. 75193); and which light chains are encoded by an expression vector designated CD4-kLC-pRcCMV (ATCC Accession No. 75194), which CD4-IgG2 fusion protein retards attachment of HIV-1 to the CD4+ cell by retarding binding of the HIV-1 gp120 envelope glycoprotein to CD4 on the surface of the CD4+ cell, the amount of the CD4-IgG2 fusion protein being effective to inhibit HIV-1 infection of the CD4+ cell; and (b) an amount of the peptide which retards gp41 from adopting a conformation capable of mediating fusion of HIV-1 to a CD4+ cell by binding noncovalently to an epitope on a gp41 fusion intermediate, wherein the peptide that retards gp41 comprises a portion of the gp41 extracellular domain, the amount of the peptide being effective to inhibit HIV-1 infection of the CD4+ cell, so as to thereby inhibit HIV-1 infection of the CD4+ cell.

12. The method of claim 11, wherein the CD4+ cell is present in a subject and the contacting is effected by administering the compounds to the subject.

13. The composition of claim 1 wherein said admixture synergistically inhibits HIV-1 infection of the CD4+ cell.

14. The method of claim 9, wherein contacting the CD4+ cell with said composition synergistically inhibits HIV-1 infection of the CD4+ cell.

15. The method of claim 11, wherein contacting the CD4+ cell with (a) the fusion protein and (b) the peptide synergistically inhibits HIV-1 infection of the CD4+ cell.

* * * * *

UNITED STATES PATENT AND TRADEMARK OFFICE
CERTIFICATE OF CORRECTION

PATENT NO. : 6,692,745 B2 Page 1 of 1
APPLICATION NO. : 09/493346
DATED : February 17, 2004
INVENTOR(S) : William C. Olson et al.

It is certified that error appears in the above-identified patent and that said Letters Patent is hereby corrected as shown below:

Section (73) on the Title page of the patent which currently indicates the Assignee name as "Arogenics Pharmaceuticals, Inc." should read as follows:

--(73) Assignee: Progenics Pharmaceuticals, Inc.,
Tarrytown, NY (US) --

Signed and Sealed this

Fifth Day of June, 2007

JON W. DUDAS
*Director of the United States Patent and Trademark Office*